United States Patent
Haimov et al.

(10) Patent No.: US 11,608,318 B2
(45) Date of Patent: Mar. 21, 2023

(54) SOLID STATE FORMS OF OMECAMTIV MECARBIL AND OMECAMTIV MECARBIL DIHCL

(71) Applicant: ASSIA CHEMICAL INDUSTRIES LTD., Petach Tikva (IL)

(72) Inventors: Elvira Haimov, Rishon LeZion (IL); Doron Rudik, Modi'in (IL); Maytal Piran, Rishon le Zion (IL)

(73) Assignee: ASSIA CHEMICAL INDUSTRIES LTD., Petach Tikva (IL)

( * ) Notice: Subject to any disclaimer, the term of this patent is extended or adjusted under 35 U.S.C. 154(b) by 234 days.

(21) Appl. No.: 17/259,591

(22) PCT Filed: Jul. 11, 2019

(86) PCT No.: PCT/US2019/041278
§ 371 (c)(1),
(2) Date: Jan. 12, 2021

(87) PCT Pub. No.: WO2020/014406
PCT Pub. Date: Jan. 16, 2020

(65) Prior Publication Data
US 2021/0317085 A1    Oct. 14, 2021

Related U.S. Application Data

(60) Provisional application No. 62/697,096, filed on Jul. 12, 2018.

(51) Int. Cl.
*C07D 213/75*    (2006.01)

(52) U.S. Cl.
CPC ........ *C07D 213/75* (2013.01); *C07B 2200/13* (2013.01)

(58) Field of Classification Search
CPC .......................... C07D 213/75; C07B 2200/13
See application file for complete search history.

(56) References Cited

U.S. PATENT DOCUMENTS

2016/0016906 A1*    1/2016   Cui .................. A61K 9/2054
                                                      544/360

FOREIGN PATENT DOCUMENTS

WO         2014152236 A1      9/2014

OTHER PUBLICATIONS

Javoor et al. "Cocrystals: A Review of Recent Trends in Pharmaceutical and Material Science Applications", Materials Science Research India, vol. 14, No. 1., Jun. 28, 2017, pp. 9-18.
International Search Report and Written Opinion of the International Searching Authority issued in corresponding Int'l Appl. No. PCT/US2019/041278 dated Oct. 14, 2019 (13 pages).

* cited by examiner

*Primary Examiner* — Timothy R Rozof
(74) *Attorney, Agent, or Firm* — Carter, DeLuca & Farrell LLP

(57) ABSTRACT

The present disclosure relates to solid state forms of Omecamtiv mecarbil and Omecamtiv mecarbil diHCl, processes for preparation thereof, pharmaceutical compositions thereof, and methods of use thereof.

16 Claims, 9 Drawing Sheets

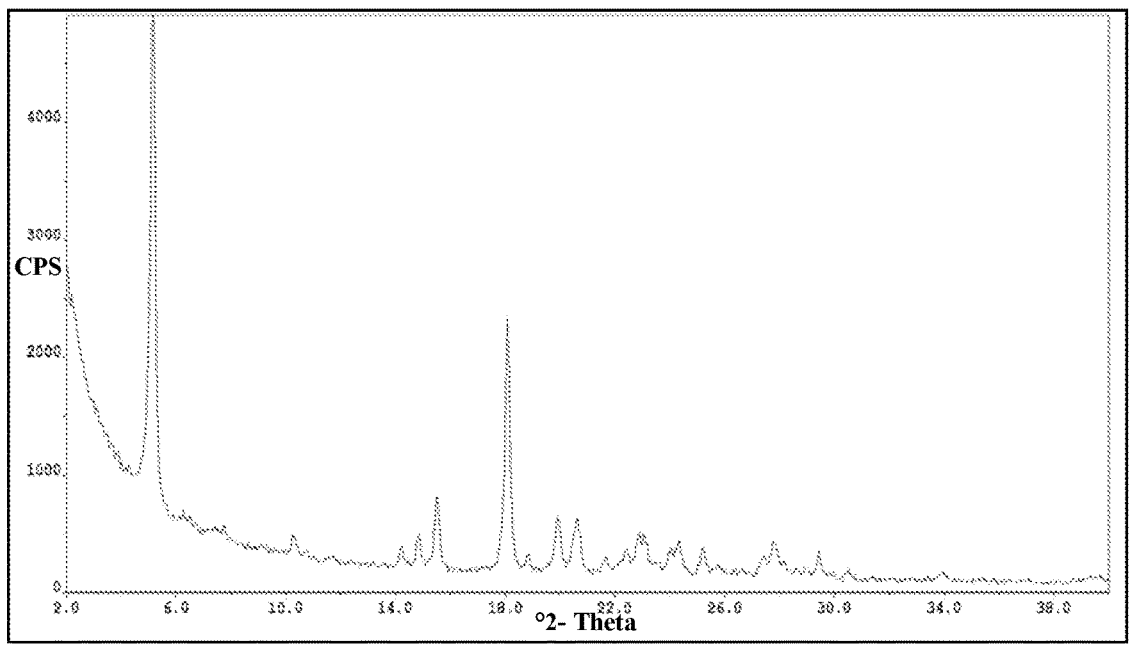
Figure 6. XRPD pattern of form O-1 of Omecamtiv mecarbil
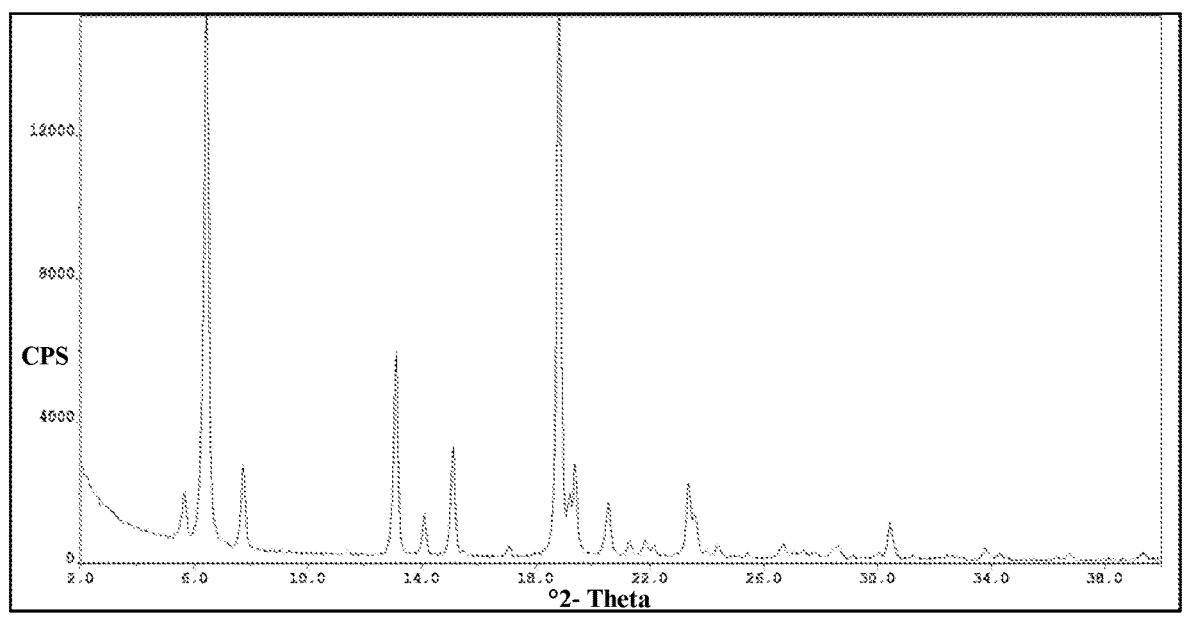
Figure 7. XRPD pattern of form O-2 of Omecamtiv mecarbil

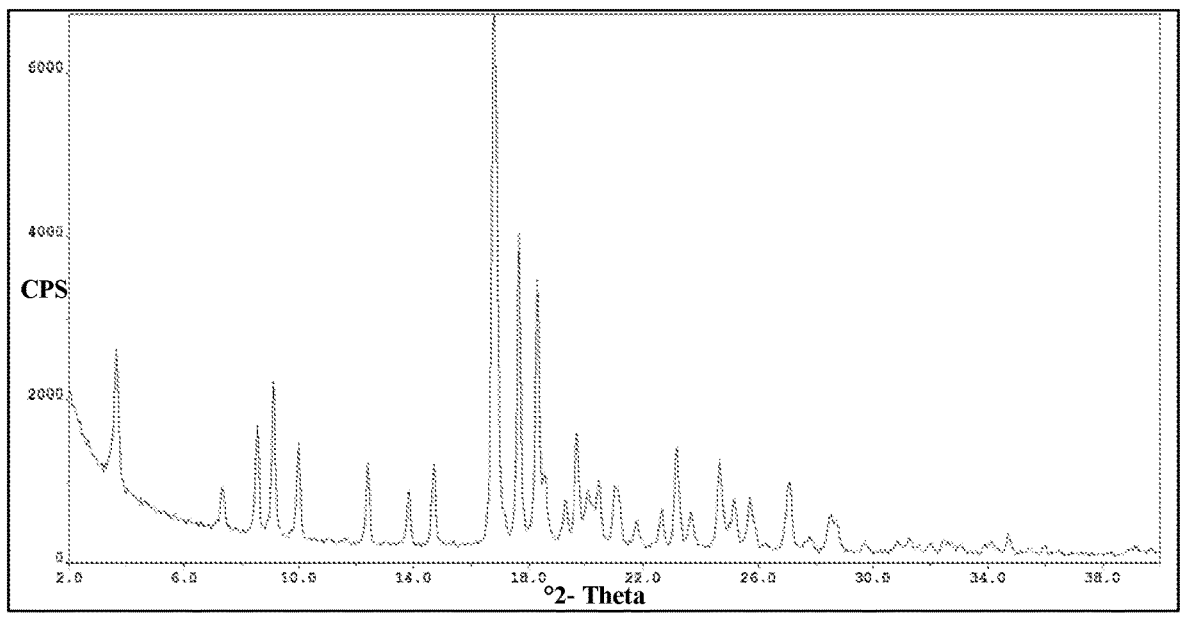
Figure 8. XRPD pattern of form O-3 of Omecamtiv mecarbil
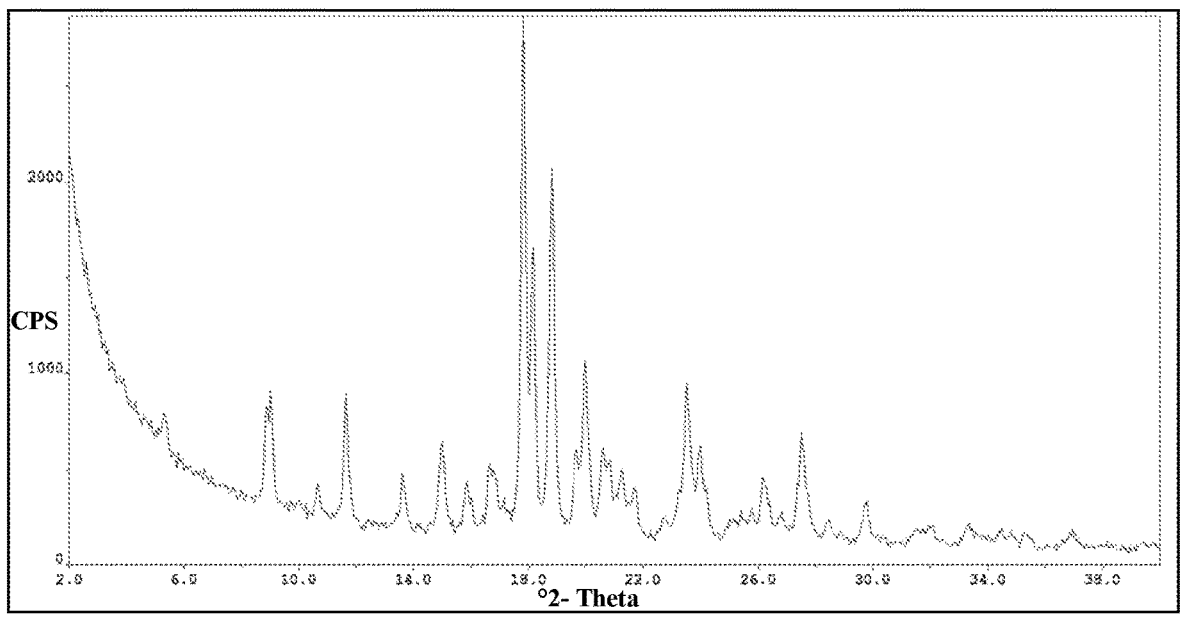
Figure 9. XRPD pattern of form O-4 of Omecamtiv mecarbil

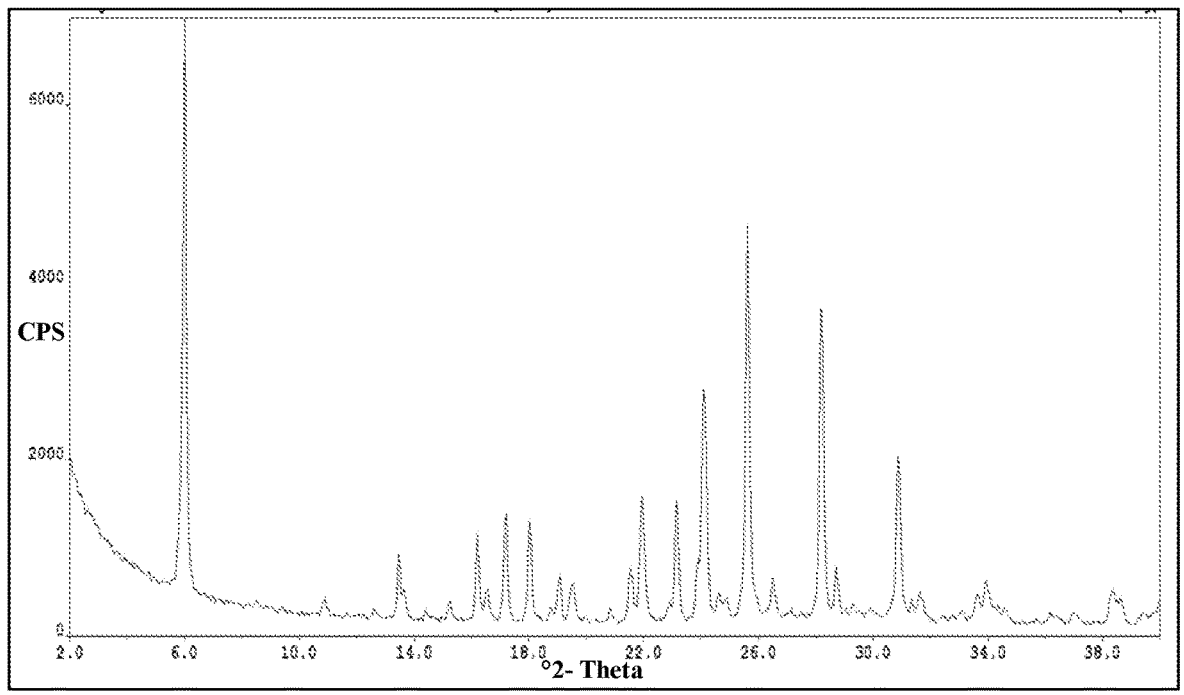
Figure 10. XRPD pattern of form O-S1 of Omecamtiv mecarbil diHCl
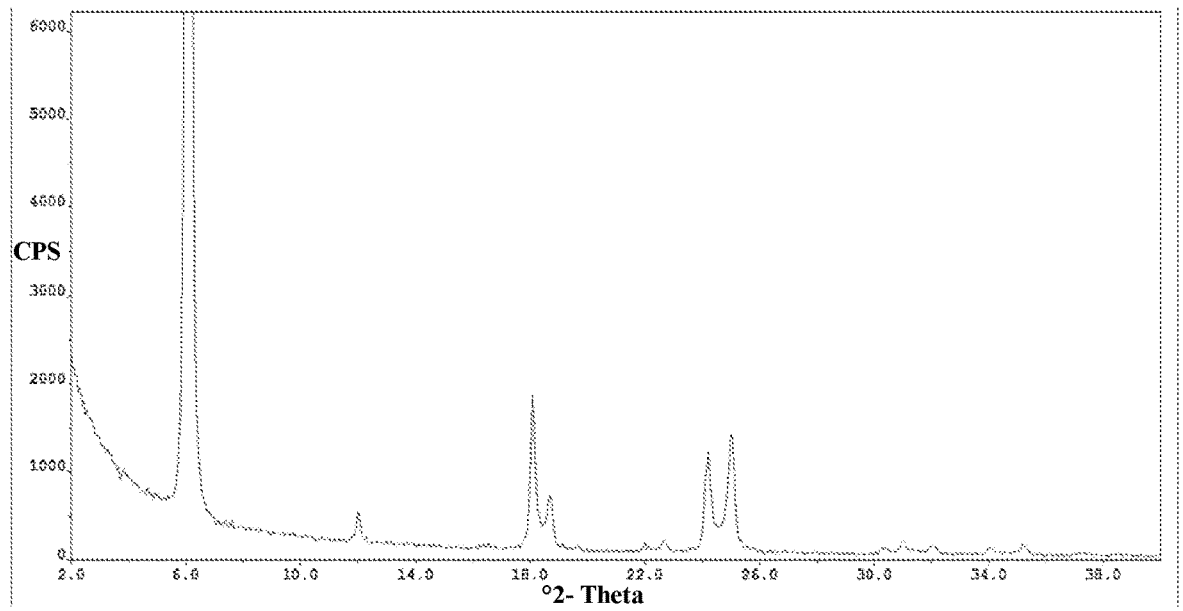
Figure 11. XRPD pattern of form O-S2 of Omecamtiv mecarbil diHCl

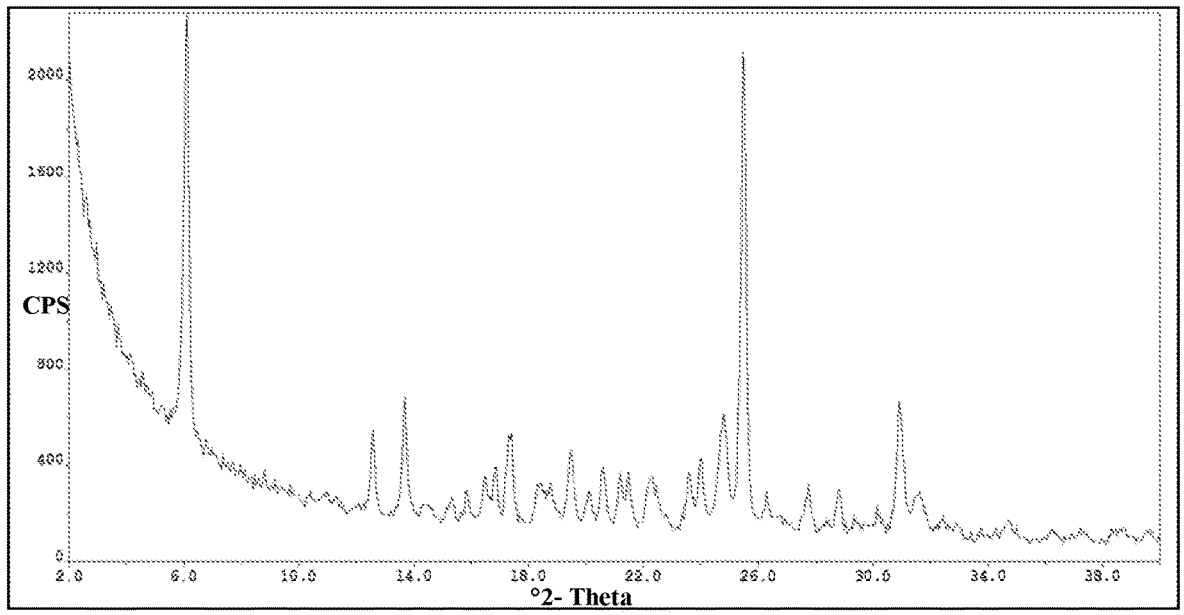
Figure 12. XRPD pattern of form O-S3 of Omecamtiv mecarbil diHCl
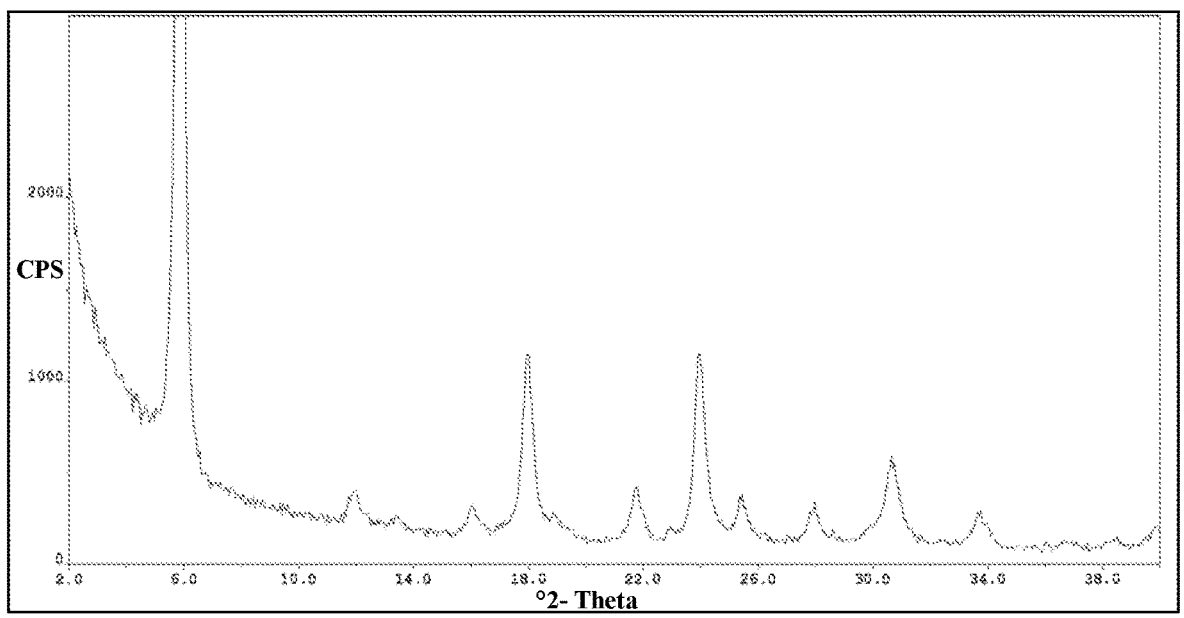
Figure 13. XRPD pattern of form O-S4 of Omecamtiv mecarbil diHCl

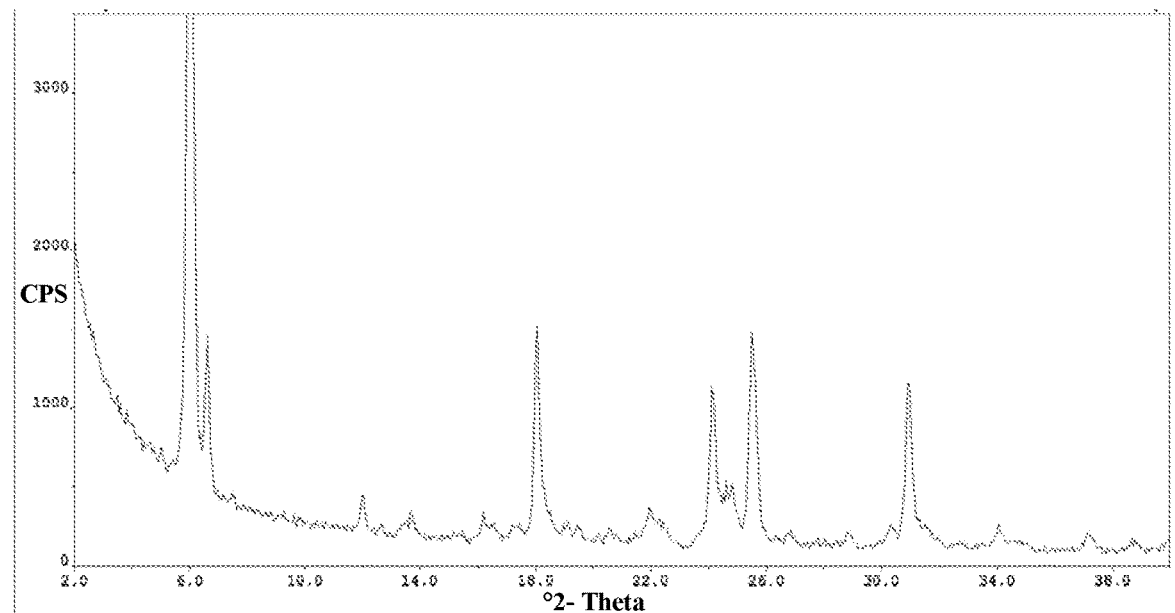
Figure 14. XRPD pattern of form O-S5 of Omecamtiv mecarbil diHCl
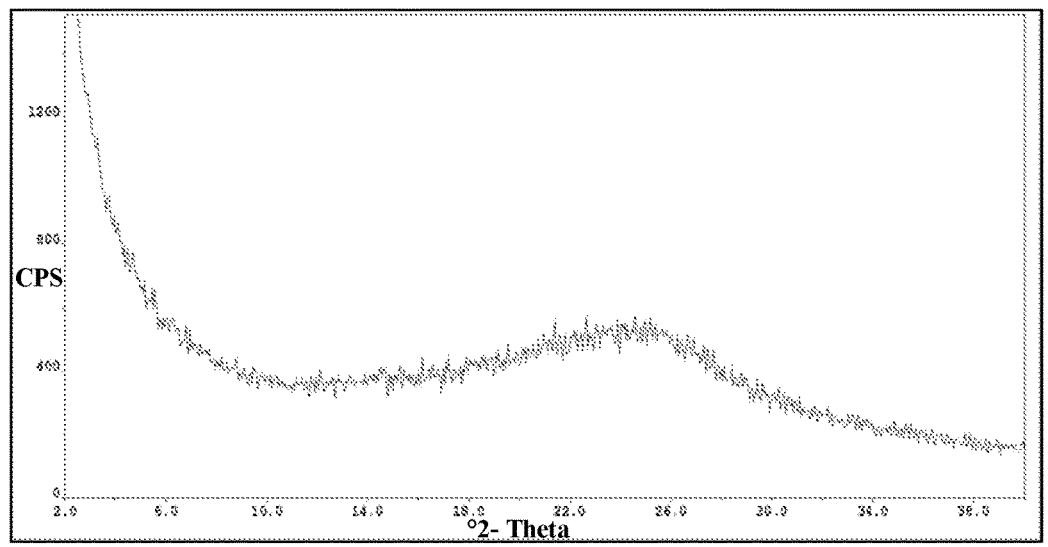
Figure 15. XRPD pattern of amorphous Omecamtiv mecarbil diHCl (prepared according to example 17)

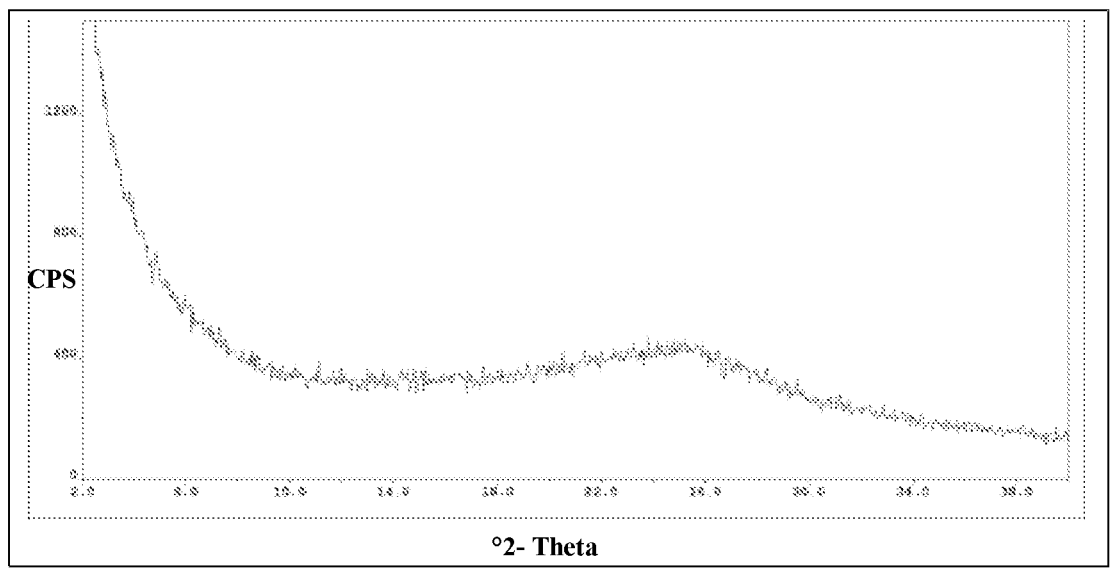
Figure 16. XRPD pattern of amorphous Omecamtiv mecarbil diHCl (prepared according to example 18)
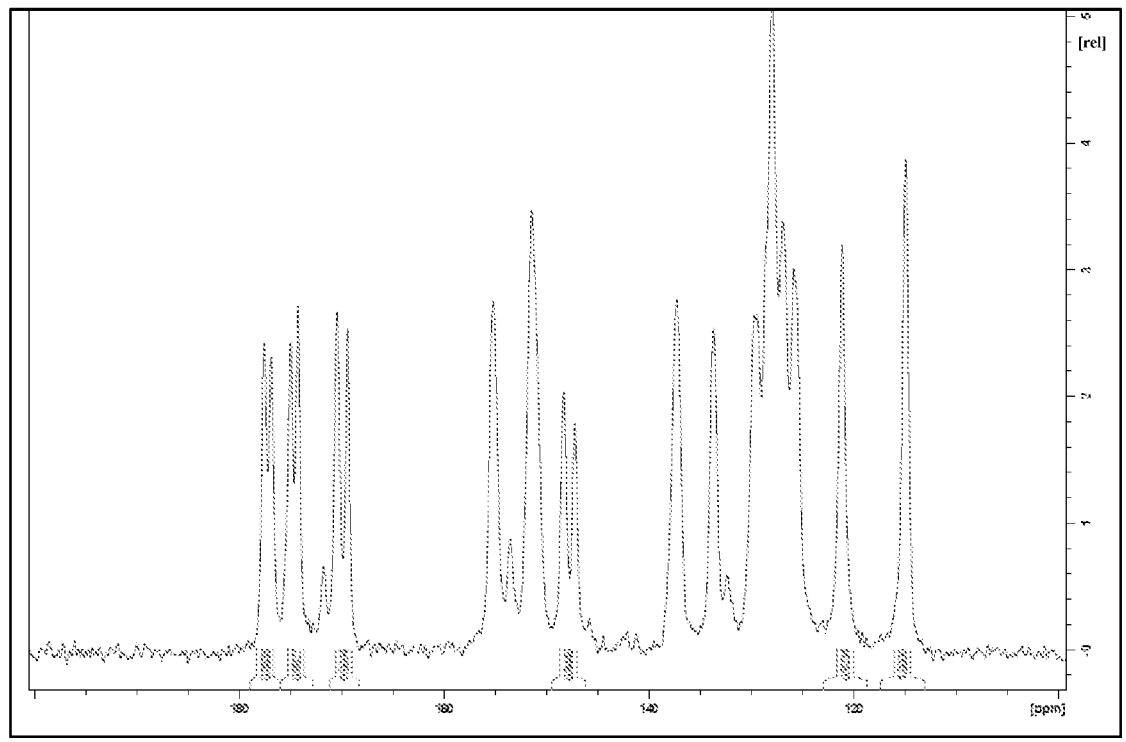
Figure 17. solid state $^{13}$C NMR of form OCC-1 of Citric Omecamtiv mecarbil diHCl

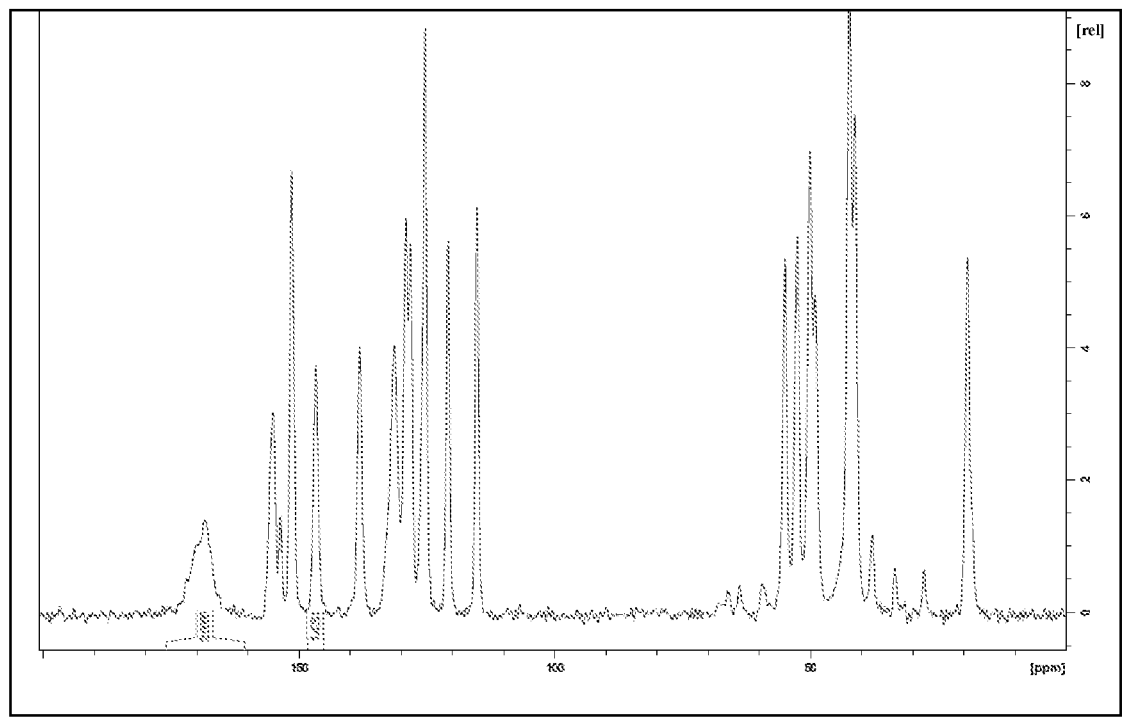
Figure 18. solid state $^{13}$C NMR of form OCM-3 of Malonic Omecamtiv mecarbil diHCl

SOLID STATE FORMS OF OMECAMTIV MECARBIL AND OMECAMTIV MECARBIL DIHCL

CROSS REFERENCE TO RELATED APPLICATIONS

This application is a National Stage of, and claims priority to and the benefit of, International Patent Application No. PCT/US2019/041278 filed Jul. 11, 2019, which, in turn, claims the benefit of, and priority to, U.S. Provisional Patent Application No. 62/697,096, filed Jul. 12, 2018, the entire disclosures of each of which are incorporated by reference herein.

TECHNICAL FIELD

The present disclosure relates to solid state forms of Omecamtiv mecarbil and Omecamtiv mecarbil diHCl, processes for preparation thereof, pharmaceutical compositions thereof, and methods of use thereof.

BACKGROUND

Omecamtiv mecarbil, methyl 4-[[2-fluoro-3-[(6-methylpyridin-3-yl)carbamoylamino]phenyl]methyl]piperazine-1-carboxylate, has the following formula;

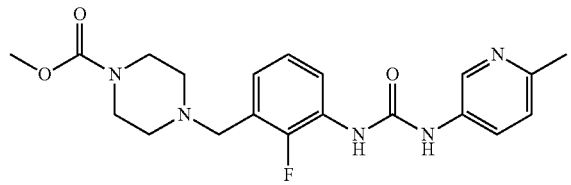

Omecamtiv mecarbil is a cardiac-specific myosin activator. It is being studied for a potential role in the treatment of heart failure. Omecamtiv mecarbil is described in U.S. Pat. No. 7,507,735. U.S. Patent Application Publication No. 2016/016906 describes a diHCl monohydrate salt of Omecamtiv mecarbil.

Polymorphism, the occurrence of different crystal forms, is a property of some molecules and molecular complexes. A single compound, like Omecamtiv mecarbil diHCl, may give rise to a variety of polymorphs having distinct crystal structures and physical properties like melting point (mp), thermal behaviors (e.g. measured by thermogravimetric analysis— "TGA", or differential scanning calorimetry— "DSC"), X-ray powder diffraction (XRPD) pattern, infrared absorption fingerprint, Raman absorption fingerprint, and solid state (13C-) NMR spectrum. One or more of these techniques may be used to distinguish different polymorphic forms of a compound.

Different salts and solid state forms (including solvated forms and co-crystals) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new solid state forms, solvates and co-crystals of a pharmaceutical product can provide materials having desirable processing properties, such as ease of handling, ease of processing, storage stability, and ease of purification or as desirable intermediate crystal forms that facilitate conversion to other salts or polymorphic forms. New polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life. For at least these reasons, there is a need for additional solid state forms (including solvated forms and co-crystals) of Omecamtiv mecarbil and Omecamtiv mecarbil diHCl.

SUMMARY OF THE DISCLOSURE

The present disclosure relates to solid state forms of Omecamtiv mecarbil and Omecamtiv mecarbil diHCl, to processes for preparation thereof, and to pharmaceutical compositions thereof.

The present disclosure relates to the use of the solid state forms of Omecamtiv mecarbil and Omecamtiv mecarbil diHCl for preparing other solid state forms of Omecamtiv mecarbil diHCl, Omecamtiv mecarbil and/or other salts of Omecamtiv mecarbil and solid state forms thereof.

The present disclosure further provides solid state forms of Omecamtiv mecarbil and/or Omecamtiv mecarbil diHCl for use in the preparation of other solid state forms of Omecamtiv mecarbil diHCl, Omecamtiv mecarbil and/or other salts of Omecamtiv mecarbil and solid state forms thereof.

The present disclosure also encompasses the use of the described solid state forms of Omecamtiv mecarbil diHCl and/or Omecamtiv mecarbil for the preparation of pharmaceutical compositions and/or formulations. The present disclosure further encompasses the described solid state forms of Omecamtiv mecarbil diHCl and/or Omecamtiv mecarbil for use in the preparation of pharmaceutical compositions and/or formulations for use in medicine, preferably for the treatment of heart failure.

In another aspect, the present disclosure provides pharmaceutical compositions comprising the solid state forms according to the present disclosure.

In yet another embodiment, the present disclosure encompasses pharmaceutical formulations comprising the described solid state forms of Omecamtiv mecarbil diHCl and/or Omecamtiv mecarbil, or of pharmaceutical compositions comprising the solid state forms of Omecamtiv mecarbil diHCl and/or Omecamtiv mecarbil, and at least one pharmaceutically acceptable excipient.

The present disclosure further encompasses processes to prepare said pharmaceutical formulations comprising combining the solid state forms of Omecamtiv mecarbil diHCl and/or Omecamtiv mecarbil as described herein; or pharmaceutical compositions comprising it and at least one pharmaceutically acceptable excipient.

The solid state forms as defined herein as well as the pharmaceutical compositions or formulations thereof may be used as medicaments, particularly for the treatment heart failure.

The present disclosure also provides methods of treating heart failure comprising administering a therapeutically effective amount of one or more of the solid state forms of Omecamtiv mecarbil and/or Omecamtiv mecarbil diHCl of the present disclosure, or at least one of the above pharmaceutical compositions or formulations, to a subject suffering from heart failure, or otherwise in need of the treatment.

The present disclosure also provides the uses of the solid state forms of Omecamtiv mecarbil diHCl and/or Omecamtiv mecarbil of the present disclosure, or at least one of the above pharmaceutical compositions or formulations, for the manufacture of medicaments for treating heart failure.

BRIEF DESCRIPTION OF THE DRAWING

FIG. 6 shows an X-ray powder diffraction (XRPD) pattern of form O-1 of Omecamtiv mecarbil.

FIG. 7 shows an X-ray powder diffraction (XRPD) pattern of form O-2 of Omecamtiv mecarbil.

FIG. 8 shows an X-ray powder diffraction (XRPD) pattern of form O-3 of Omecamtiv mecarbil.

FIG. 9 shows an X-ray powder diffraction (XRPD) pattern of form O-4 of Omecamtiv mecarbil.

FIG. 10 shows an X-ray powder diffraction (XRPD) pattern of form O-S1 of Omecamtiv mecarbil diHCl.

FIG. 11 shows an X-ray powder diffraction (XRPD) pattern of form O-S2 of Omecamtiv mecarbil diHCl.

FIG. 12 shows an X-ray powder diffraction (XRPD) pattern of form O-S3 of Omecamtiv mecarbil diHCl.

FIG. 13 shows an X-ray powder diffraction (XRPD) pattern of form O-S4 of Omecamtiv mecarbil diHCl.

FIG. 14 shows an X-ray powder diffraction (XRPD) pattern of form O-S5 of Omecamtiv mecarbil diHCl.

FIG. 15 shows an X-ray powder diffraction (XRPD) patterns of amorphous Omecamtiv mecarbil diHCl; as obtained by example 17.

FIG. 16 shows an X-ray powder diffraction (XRPD) patterns of amorphous Omecamtiv mecarbil diHCl; as obtained by example 18.

FIG. 17 shows solid state $^{13}$C NMR of form OCC-1 of Citric Omecamtiv mecarbil diHCl.

FIG. 18 shows solid state $^{13}$C NMR of form OCM-3 of Malonic Omecamtiv mecarbil diHCl.

DETAILED DESCRIPTION OF THE DISCLOSURE

Figure 1:
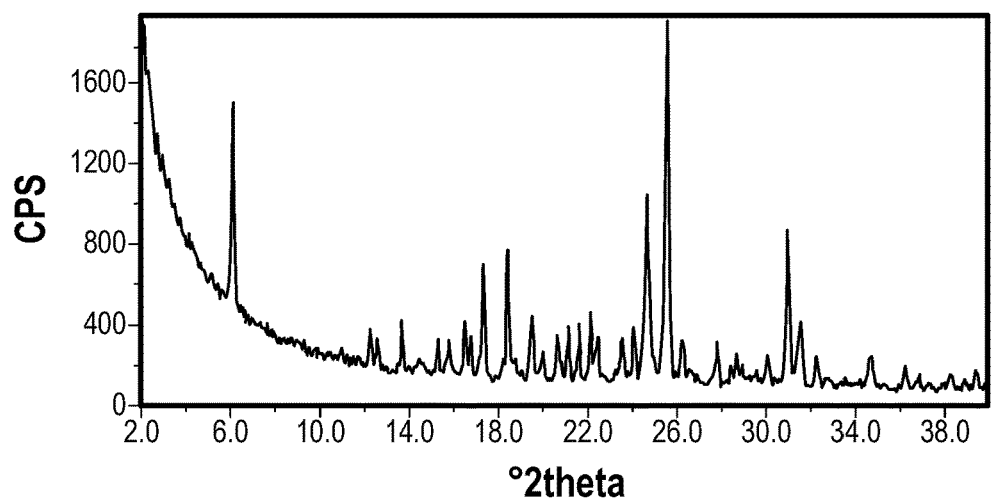
FIG. 1 shows an X-ray powder diffraction (XRPD) pattern of form OCG-1 of Glycolic Omecamtiv mecarbil diHCl.

The present disclosure relates to solid state forms of Omecamtiv mecarbil and Omecamtiv mecarbil diHCl, to processes for preparation thereof and to pharmaceutical compositions comprising these solid state forms and/or combinations thereof. The disclosure also relates to the conversion of Omecamtiv mecarbil and/or Omecamtiv mecarbil diHCl of the present disclosure to other solid state forms of Omecamtiv mecarbil diHCl, Omecamtiv mecarbil and solid state forms thereof.

The solid state forms of Omecamtiv mecarbil and Omecamtiv mecarbil diHCl, according to the present disclosure, may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents, adhesive tendencies and advantageous processing and handling characteristics such as compressibility, and bulk density.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

A crystal form of Omecamtiv mecarbil and Omecamtiv mecarbil diHCl referred to herein as being characterized by graphical data "as depicted in" a Figure will thus be understood to include any crystal forms of the Omecamtiv mecarbil/Omecamtiv mecarbil diHCl, characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, solid state of Omecamtiv mecarbil or Omecamtiv mecarbil diHCl described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject solid state form. Accordingly, in some embodiments of the disclosure, the described solid state forms of Omecamtiv mecarbil/Omecamtiv mecarbil diHCl may contain from about 1% to about 20% (w/w), from about 5% to about 20% (w/w), or from about 5% to about 10% (w/w) of one or more other solid state forms of Omecamtiv mecarbil/Omecamtiv mecarbil diHCl.

As used herein, unless stated otherwise, XRPD peaks reported herein are preferably measured using CuKα radiation, λ=1.5418 Å. XRPD peaks reported herein are measured using CuK α radiation, λ=1.5418 Å, at a temperature of 25±3° C.

As used herein, unless stated otherwise, $^{13}$C NMR reported herein are measured at 125 MHz at a magic angle spinning frequency $\omega_r/2\pi$=11 kHz, preferably at a temperature of at 293 K±3° C.

As used herein, the term "isolated" in reference to solid state forms of Omecamtiv mecarbil and Omecamtiv mecarbil diHCl of the present disclosure corresponds to solid state forms of Omecamtiv mecarbil and Omecamtiv mecarbil diHCl that is physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, or about 10 to about 18 hours, typically about 16 hours.

The amount of solvent employed in a chemical process, e.g., a reaction or a crystallization may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

As used herein, the term "reduced pressure" refers to a pressure of about 10 mbar to about 500 mbar.

As used herein and unless indicated otherwise, the term "ambient conditions" refer to atmospheric pressure, 22-24° C.

The present disclosure comprises a crystalline form of Glycolic Omecamtiv mecarbil diHCl designated OCG-1. The crystalline form OCG-1 of Glycolic Omecamtiv mecarbil diHCl can be characterized by data selected from one or more of the following: an XRPD pattern having peaks at 6.1, 17.3, 18.4, 24.6 and 25.6 degrees 2-theta±0.2 degrees 2-theta; an XRPD pattern substantially as depicted in FIG. 1; and combinations of these data.

Crystalline form OCG-1 of Glycolic Omecamtiv mecarbil diHCl may be further characterized by an XRPD pattern having peaks at 6.1, 17.3, 18.4, 24.6 and 25.6 degrees two theta±0.2 degrees two theta, and also having one, two, three, four or five additional peaks selected from 13.7, 16.5, 19.5, 21.5 and 31.0 degrees two theta±0.2 degrees two theta.

Figure 2:
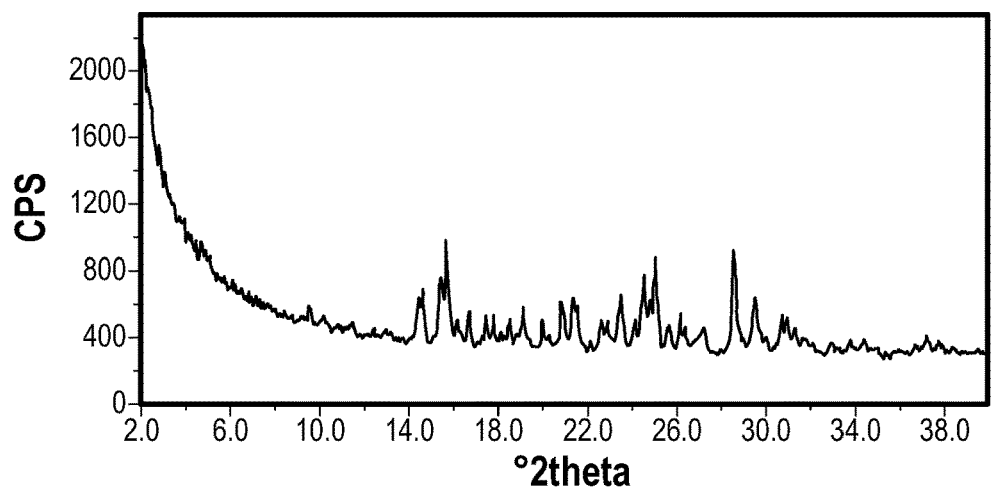
FIG. 2 shows an X-ray powder diffraction (XRPD) pattern of form OCC-1 of Citric Omecamtiv mecarbil diHCl.

In another aspect, the present disclosure comprises a crystalline form of Citric Omecamtiv mecarbil diHCl designated OCC-1. The crystalline form OCC-1 of Citric Omecamtiv mecarbil diHCl can be characterized by data selected from one or more of the following: an XRPD pattern having peaks at 14.6, 15.6, 16.7, 24.5 and 25.1 degrees two theta±0.2 degrees two theta; an XRPD pattern substantially as depicted in FIG. 2; and combinations of these data.

Crystalline form OCC-1 of Citric Omecamtiv mecarbil diHCl may be further characterized by an XRPD pattern having peaks at 14.6, 15.6, 16.7, 24.5 and 25.1 degrees two theta±0.2 degrees two theta, and also having one, two, three, four or five additional peaks selected from 15.4, 19.2, 20.9, 23.5 and 29.6 degrees two theta±0.2 degrees two theta.

Crystalline form OCC-1 of Citric Omecamtiv mecarbil diHCl may alternatively or additionally be characterized by data selected from one or more of the following: a solid state $^{13}$C NMR spectrum with characteristic peaks at: 176.9, 174.3, 170.4, 148.3 and 133.7±2 ppm; a solid state $^{13}$C NMR spectrum having the following chemical shift absolute differences from reference peak at 177.6±2 ppm: 0.7, 3.3, 7.2, 29.3 and 43.9±2 ppm; or by solid state $^{13}$C NMR spectrum as depicted in FIG. 17; or combinations of these data.

Crystalline form OCC-1 of Citric Omecamtiv mecarbil diHCl according to the present invention is mechanically and thermodynamically stable (i.e., it is steady under stressed conditions (e.g., high temperature and relative humidity)). Pharmaceutical molecules may display solid to solid phase transformations and transformations between polymorphs; which may detected by exposure of the solid state form to stress conditions of e.g., high temperature and high relative humidity. In particular, crystalline form OCC-1 of Citric Omecamtiv mecarbil diHCl according to the present invention has shown to be thermodynamically and mechanically stable.

Figure 3:
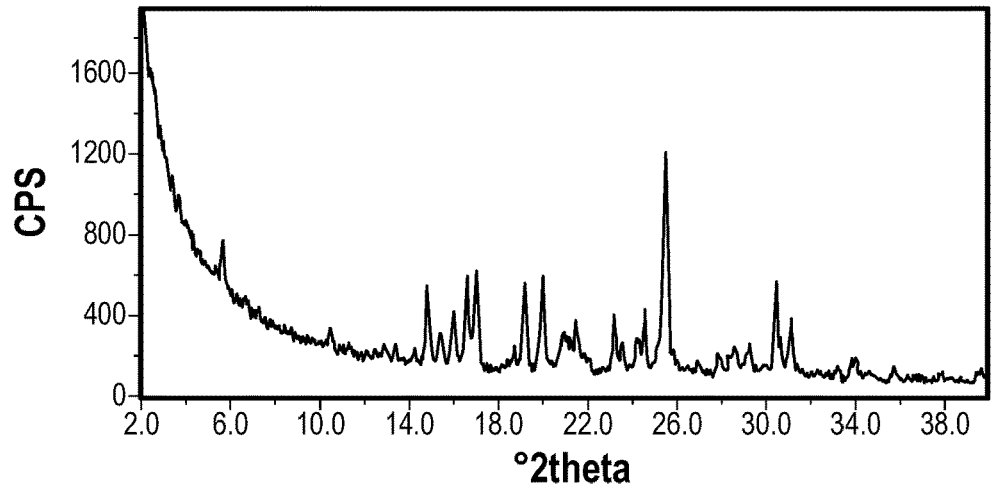
FIG. 3 shows an X-ray powder diffraction (XRPD) pattern of form OCM-1 of Malic Omecamtiv mecarbil diHCl.

In another aspect, the present disclosure comprises a crystalline form of Malic Omecamtiv mecarbil diHCl designated form OCM-1. The crystalline form OCM-1 of Malic Omecamtiv mecarbil diHCl can be characterized by data selected from one or more of the following: an XRPD pattern having peaks at 15.0, 17.2, 19.2, 20.0 and 25.5 degrees two theta±0.2 degrees two theta; an XRPD pattern substantially as depicted in FIG. 3; and combinations of these data.

Crystalline form OCM-1 of Malic Omecamtiv mecarbil diHCl may be further characterized by an XRPD pattern having peaks at 15.0, 17.2, 19.2, 20.0 and 25.5 degrees two theta±0.2 degrees two theta, and also having one, two, three, four or five additional peaks selected from 16.0, 16.6, 23.2, 24.6 and 30.5 degrees two theta±0.2 degrees two theta.

Figure 4:
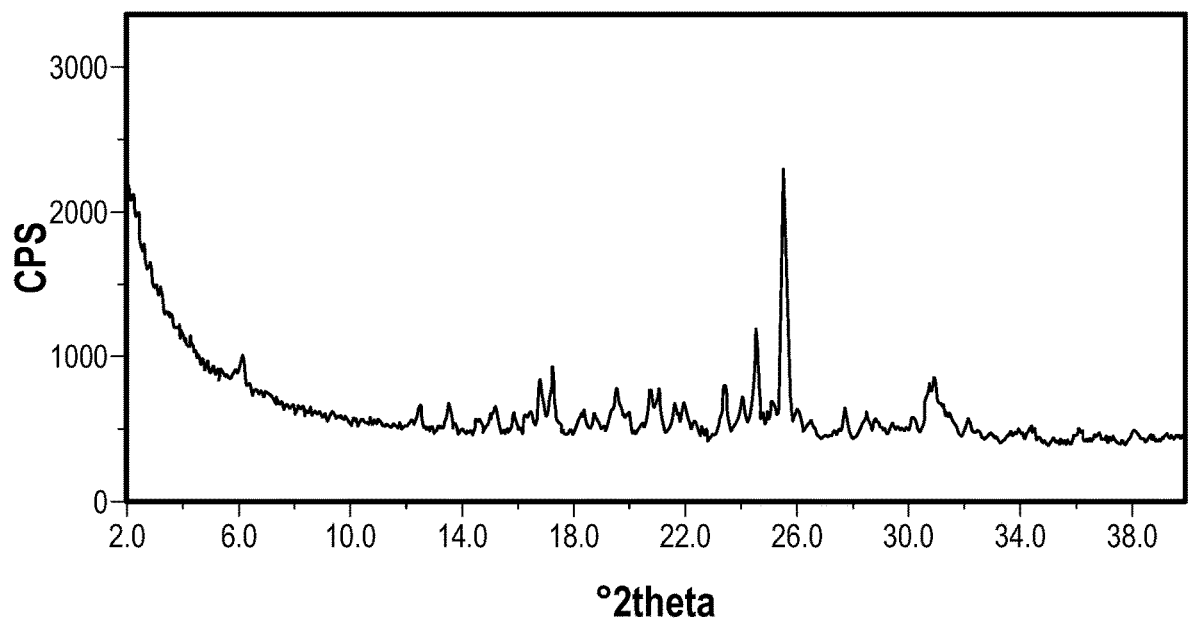
FIG. 4 shows an X-ray powder diffraction (XRPD) pattern of form OCM-2 of Malic Omecamtiv mecarbil diHCl.

In another aspect, the present disclosure comprises a crystalline form of Malic Omecamtiv mecarbil diHCl designated form OCM-2. The crystalline form OCM-2 of Malic Omecamtiv mecarbil diHCl can be characterized by data selected from one or more of the following: an XRPD pattern having peaks at 16.9, 17.3, 23.5, 24.6 and 25.6 degrees two theta±0.2 degrees two theta; an XRPD pattern substantially as depicted in FIG. 4; and combinations of these data.

Crystalline form OCM-2 of Malic Omecamtiv mecarbil diHCl may be further characterized by an XRPD pattern having peaks at 16.9, 17.3, 23.5, 24.6 and 25.6 degrees two theta±0.2 degrees two theta, and also having one, two, three, four or five additional peaks selected from 19.6, 20.8, 21.1, 23.5 and 27.8 degrees two theta±0.2 degrees two theta.

Figure 5:
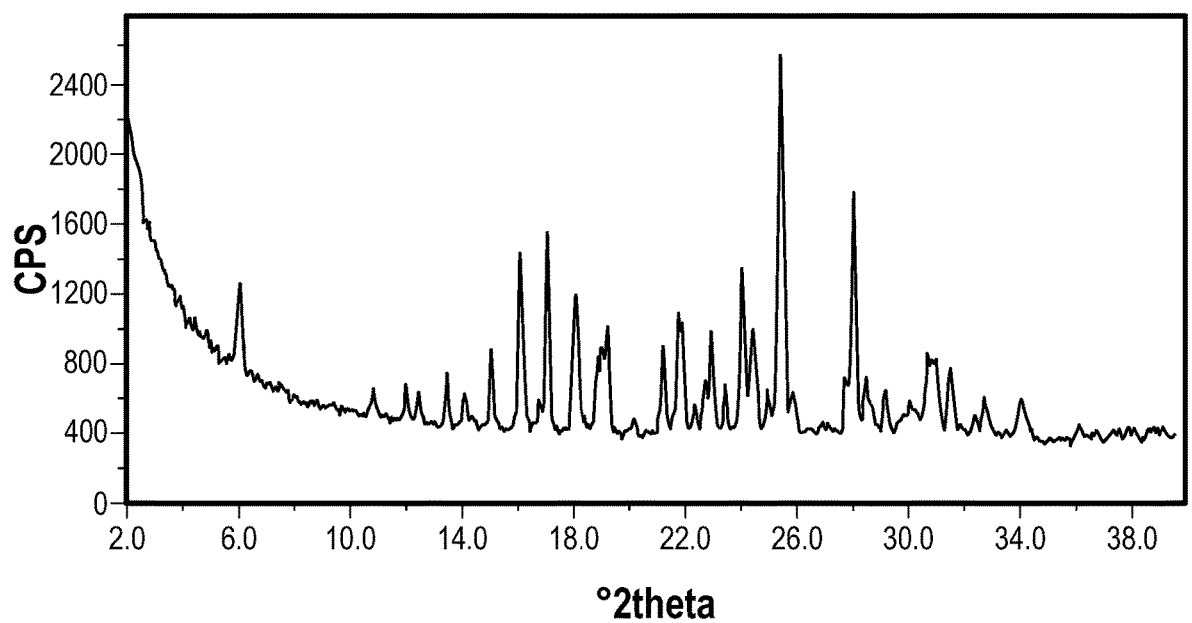
FIG. 5 shows an X-ray powder diffraction (XRPD) pattern of form OCM-3 of Malonic Omecamtiv mecarbil diHCl.

In another aspect, the present disclosure comprises a crystalline form of Malonic Omecamtiv mecarbil diHCl designated form OCM-3. The crystalline form OCM-3 of Malonic Omecamtiv mecarbil diHCl can be characterized by data selected from one or more of the following: an XRPD pattern having peaks at 6.0, 16.2, 17.2, 24.3 and 25.7 degrees two theta±0.2 degrees two theta; an XRPD pattern substantially as depicted in FIG. 5; and combinations of these data.

Crystalline form OCM-3 of Malonic Omecamtiv mecarbil diHCl may be further characterized by an XRPD pattern having peaks at 6.0, 16.2, 17.2, 24.3 and 25.7 degrees two theta±0.2 degrees two theta, and also having one, two, three, four or five additional peaks selected from 12.1, 18.2, 19.0, 21.4 and 28.3 degrees two theta±0.2 degrees two theta.

Crystalline form OCM-3 of Malonic Omecamtiv mecarbil diHCl may alternatively or additionally be characterized by data selected from one or more of the following: a solid state $^{13}$C NMR spectrum with characteristic peaks at: 146.8, 138.1, 131.4, 121.0 and 115.3±2 ppm; a solid state $^{13}$C NMR spectrum having the following chemical shift absolute differences from reference peak at 168.5 ppm±2 ppm: 21.7, 30.4, 37.1, 47.5 and 53.3±2 ppm; or by solid state $^{13}$C NMR spectrum as depicted in FIG. 18; or combinations of these data.

Crystalline form OCM-3 of Malonic Omecamtiv mecarbil diHCl according to the present invention is mechanically and thermodynamically stable. Pharmaceutical molecules may display solid to solid phase transformations and transformations between polymorphs; which may detected by exposure of the solid state form to stress conditions of e.g., high temperature and high relative humidity. In particular, crystalline form OCM-3 of Malonic Omecamtiv mecarbil diHCl according to the present invention has shown to be thermodynamically and mechanically stable.

Particularly, forms OCG-1, OCC-1, OCM-1, OCM-2 and OCM-3 as described in any embodiment are cocrystals of Omecamtiv mecarbil diHCl with the respective acid In another aspect of the present invention, there is provided a process for preparing a crystalline form of Omecamtiv mecarbil diHCl selected from glycolic Omecamtiv mecarbil diHCl, citric Omecamtiv mecarbil diHCl, malic Omecamtiv mecarbil diHCl, and malonic Omecamtiv mecarbil diHCl, wherein the process comprises the following steps:
  (i) providing a mixture comprising Omecamtiv mecarbil diHCl and the appropriate acid (i.e. glycolic acid, citric acid, malic acid, or malonic acid) in water;
  (ii) optionally stirring the mixture;
  (iii) at least partially removing the water, and optionally adding a non-protic solvent; and
  (vi) isolating the crystalline form.

Preferably, step (i) comprises preparing a solution of Omecamtiv mecarbil diHCl in water, and a solution of the appropriate acid in water, and combining the two solutions, thereby forming a solution. Preferably, the water employed in the process is distilled, more preferably double distilled.

The crystalline form of Omecamtiv mecarbil diHCl prepared in the above process may be Glycolic Omecamtiv mecarbil diHCl form OCG-1, Citric Omecamtiv mecarbil diHCl form OCC-1, Malic Omecamtiv mecarbil diHCl form OCM-1 or OCM-2, and Malonic Omecamtiv mecarbil diHCl OCM-3.

Preferably, for the preparation of any of the Glycolic Omecamtiv mecarbil diHCl form OCG-1, Citric Omecamtiv mecarbil diHCl form OCC-1, Malic Omecamtiv mecarbil diHCl form OCM-1 or OCM-2, and Malonic Omecamtiv mecarbil diHCl OCM-3 according to any of the embodiments disclosed herein, about 1 equivalent (preferably about 1.0 to about 1.2, more particularly about 1.0 to about 1.1 equivalent) of the acid based on the Omecamtiv mecarbil is used. Preferably, the stirring step (ii) according to any of the embodiments is carried out at room temperature overnight.

Preferably, step (iii) of any of the embodiments comprises heating to a temperature of about 45° C. to about 65° C., more preferably about 50° C. to about 60° C., and most preferably about 55° C., preferably under reduced pressure. The heating may be carried out for a time sufficient to obtain a solid.

After the water removal step, a non-protic solvent may be added to the product. The non-protic solvent can be any suitable solvent that enables trituration or suspension of the product from the water removal step. Preferably the non-protic solvent is an ether, preferably an ether such as tert-butyl methyl ether; an aromatic solvent such as toluene; or acetonitrile. The mixture may be stirred, preferably at room temperature, and preferably for about 8 to about 30 hours, more preferably about 10 to about 25 hours, and most preferably about 15 to about 20 hours. The resulting product may be isolated by any suitable method, such a centrifugation or filtration. Alternatively, the product may be isolated directly from the water removal step.

Form OCG-1 of Glycolic Omecamtiv mecarbil diHCl as described in any of the embodiments herein may be prepared by a process comprising:
  (i) providing a mixture comprising Omecamtiv mecarbil diHCl and glycolic acid (preferably about 1.0 to about 1.2, more particularly about 1.0 to about 1.1 equivalents) in water;
  (ii) stirring the mixture, preferably at room temperature for about 3 to about 20 hours, more preferably about 8 to about 20 hours, or about 10 to about 18 hours, and most preferably about 16 hours;
  (iii) removing the water at reduced pressure and preferably at a temperature of about 50° C. to about 60° C., and optionally adding a non-protic solvent, preferably an ether, and more preferably methyl tert-butyl ether; and
  (vi) isolating the crystalline form OCG-1 of Glycolic Omecamtiv mecarbil diHCl, preferably by filtration or centrifugation.

Form OCC-1 of Citric Omecamtiv mecarbil diHCl as described in any of the embodiments herein may be prepared by a process comprising:
  (i) providing a mixture comprising Omecamtiv mecarbil diHCl and citric acid (preferably about 1.0 to about 1.2, more particularly about 1.0 to about 1.1 equivalents) in water;
  (ii) stirring the mixture, preferably at room temperature for about 3 to about 20 hours, more preferably about 8 to about 20 hours, or about 10 to about 18 hours, and most preferably about 16 hours;
  (iii) removing the water at reduced pressure and preferably at a temperature of about 50° C. to about 60° C., and optionally adding a non-protic solvent, preferably an aromatic hydrocarbon and more particularly, toluene; and
  (vi) isolating the crystalline form OCC-1 of Citric Omecamtiv mecarbil diHCl, preferably by filtration or centrifugation.

Form OCM-1 of Malic Omecamtiv mecarbil diHCl as described in any of the embodiments herein may be prepared by a process comprising:
  (i) providing a mixture comprising Omecamtiv mecarbil diHCl and malic acid (preferably about 1.0 to about 1.2, more particularly about 1.0 to about 1.1 equivalents) in water;
  (ii) stirring the mixture, preferably at room temperature for about 3 to about 20 hours, more preferably about 8 to about 20 hours, or about 10 to about 18 hours, and most preferably about 16 hours;

(iii) removing the water at reduced pressure and preferably at a temperature of about 50° C. to about 60° C.; and (vi) isolating the crystalline form OCM-1 of Malic Omecamtiv mecarbil diHCl.

Form OCM-2 of Malic Omecamtiv mecarbil diHCl as described in any of the embodiments herein may be prepared by a process comprising:

(i) providing a mixture comprising Omecamtiv mecarbil diHCl and malic acid (preferably about 1.0 to about 1.2, more particularly about 1.0 to about 1.1 equivalents) in water;

(ii) stirring the mixture, preferably at room temperature for about 3 to about 20 hours, more preferably about 8 to about 20 hours, or about 10 to about 18 hours, and most preferably about 16 hours;

(iii) removing the water at reduced pressure and preferably at a temperature of about 50° C. to about 60° C., and optionally adding a non-protic solvent, preferably acetonitrile; and (vi) isolating the crystalline form OCM-2 of Malic Omecamtiv mecarbil diHCl, preferably by filtration or centrifugation.

Form OCM-3 of Malonic Omecamtiv mecarbil diHCl as described in any of the embodiments herein may be prepared by a process comprising:

(i) providing a mixture comprising Omecamtiv mecarbil diHCl and malonic acid (preferably about 1.0 to about 1.2, more particularly about 1.0 to about 1.1 equivalents) in water;

(ii) removing the water at reduced pressure and preferably at a temperature of about 50° C. to about 60° C., and optionally adding a non-protic solvent, preferably acetonitrile; and (vi) isolating the crystalline form OCM-3 of Malonic Omecamtiv mecarbil diHCl, preferably by filtration or centrifugation.

In a further aspect form OCM-3 of Malonic Omecamtiv mecarbil diHCl as described in any of the embodiments herein may be prepared by a process comprising:

(i) providing a mixture comprising Omecamtiv mecarbil diHCl and malonic acid in an organic solvent, preferably a non-protic solvent selected from: acetonitrile, ethyl acetate, isopropyl acetate, toluene, tert-Butyl methyl ether, dichloromethane, chloroform, and combinations thereof); and (ii) isolating the crystalline form OCM-3 of Malonic Omecamtiv mecarbil diHCl, preferably by filtration or centrifugation.

Form OCM-3 of Malonic Omecamtiv mecarbil diHCl may also be prepared by grinding Omecamtiv mecarbil diHCl with malonic acid (preferably in an amount of about 1.0 to about 1.05, and more preferably about 1.0 equivalents) in the presence of water, preferably at room temperature.

The processes according to any embodiment of the invention for preparing the crystalline forms of the present invention, particularly Glycolic Omecamtiv mecarbil diHCl form OCG-1, Citric Omecamtiv mecarbil diHCl form OCC-1, Malic Omecamtiv mecarbil diHCl form OCM-1 or OCM-2, and Malonic Omecamtiv mecarbil diHCl form OCM-3, as well as forms O-1, O-2, O-3 and O4, according to any of the embodiments disclosed herein, may further comprise combining the crystalline form with one or more pharmaceutically acceptable excipients to provide a pharmaceutical composition or formulation.

In a further aspect, the present disclosure comprises crystalline form O-1 of Omecamtiv mecarbil. The crystalline form O-1 of Omecamtiv mecarbil can be characterized by data selected from one or more of the following: an XRPD pattern having peaks at 5.1, 15.5, 18.1, 19.9 and 20.6 degrees two theta±0.2 degrees two theta; an XRPD pattern substantially as depicted in FIG. 6; and combinations of these data.

Crystalline form O-1 of Omecamtiv mecarbil may be further characterized by an XRPD pattern having peaks at 5.1, 15.5, 18.1, 19.9 and 20.6 degrees two theta±0.2 degrees two theta, and also having one, two, three, four or five additional peaks selected from 10.3, 14.2, 14.8, 23.1 and 24.3 degrees two theta±0.2 degrees two theta.

Form O-1 of Omecamtiv mecarbil may be prepared by a process comprising dissolving Omecamtiv mecarbil in an aprotic solvent (preferably selected from ethyl acetate or THF), and adding an aliphatic hydrocarbon (preferably hexane). Preferably the crystallization is carried out at a temperature of about 0° C. to about 15° C., particularly at 0° C. to about 10° C., and more preferably at 0° C. to about 5° C. The resulting precipitate is isolated, preferably by filtration or centrifugation, and the product is dried under reduced pressure, preferably at a temperature of about 40° C. to about 65° C., particularly 45° C. to about 55° C. Preferably the drying step is carried out over about 4 to about 30 hours, more preferably about 10 to about 25 hours and most preferably about 15 to about 20 hours.

The present disclosure also provides crystalline form O-2 of Omecamtiv mecarbil. The crystalline form O-2 of Omecamtiv mecarbil can be characterized by data selected from one or more of the following: an XRPD pattern having peaks at 6.5, 13.1, 15.1, 18.9 and 23.4 degrees two theta±0.2 degrees two theta; an XRPD pattern substantially as depicted in FIG. 7 and combinations of these data.

Crystalline form O-2 of Omecamtiv mecarbil may be further characterized by an XRPD pattern having peaks at 6.5, 13.1, 15.1, 18.9 and 23.4 degrees two theta±0.2 degrees two theta, and also having one, two, three, four or five additional peaks selected from 5.7, 7.8, 14.1, 19.4 and 20.6 degrees two theta±0.2 degrees two theta.

Form O-2 of Omecamtiv mecarbil may be prepared by a process comprising cooling a hot solution of Omecamtiv mecarbil in methanol or THF. Preferably, the process comprises dissolving Omecamtiv mecarbil in methanol or THF, preferably at a temperature of about 40° C. to about 80° C. The solution is cooled, preferably to room temperature to provide a precipitate, which is isolated by filtration or centrifugation.

In a further embodiment, the present disclosure comprises form O-3 of Omecamtiv mecarbil. The crystalline form O-3 of Omecamtiv mecarbil may be characterized by data selected from one or more of the following: an XRPD pattern having peaks at 3.6, 9.2, 16.8, 17.7 and 18.3 degrees two theta±0.2 degrees two theta; an XRPD pattern substantially as depicted in FIG. 8 and combinations of these data.

Crystalline form O-3 of Omecamtiv mecarbil may be further characterized by an XRPD pattern having peaks at 3.6, 9.2, 16.8, 17.7 and 18.3 degrees two theta±0.2 degrees two theta, and also having one, two, three, four or five additional peaks selected from 8.5, 10.0, 14.7, 19.7 and 23.2 degrees two theta±0.2 degrees two theta.

Form O-3 of Omecamtiv mecarbil may be prepared by a process comprising cooling a hot solution of Omecamtiv mecarbil in dioxane. Preferably, the process comprises dissolving Omecamtiv mecarbil in dioxane, preferably at a temperature of about 50° C. to about 120° C., and more preferably about 70° C. to about 110° C., and most preferably about 80° C. to about 100° C. The solution is cooled, preferably to room temperature and preferably stirred for about 1 to about 30 hours, to provide a precipitate, which is isolated by filtration or centrifugation.

The present disclosure also provides crystalline form O-4 of Omecamtiv mecarbil. The crystalline form O-4 of Omecamtiv mecarbil can be characterized by data selected from one or more of the following: an XRPD pattern having peaks at 11.7, 17.8, 18.2, 18.8 and 23.5 degrees two theta±0.2 degrees two theta; an XRPD pattern substantially as depicted in FIG. 9 and combinations of these data.

Crystalline form O-4 of Omecamtiv mecarbil may be further characterized by an XRPD pattern having peaks at 11.7, 17.8, 18.2, 18.8 and 23.5 degrees two theta±0.2 degrees two theta, and also having one, two, three, four or five additional peaks selected from 9.1, 13.6, 15.0, 20.6 and 27.6 degrees two theta±0.2 degrees two theta.

Form O-4 of Omecamtiv mecarbil may be prepared by a process comprising cooling a hot solution of Omecamtiv mecarbil in dioxane. Preferably, the process comprises dissolving Omecamtiv mecarbil in dioxane, preferably at a temperature of about 50° C. to about 120° C., and more preferably about 70° C. to about 110° C., and most preferably about 80° C. to about 100° C. The solution is cooled, preferably to room temperature and preferably stirred for about 1 to about 30 hours, to provide a precipitate, which is isolated and dried under reduced pressure. The drying is preferably carried out at about 40° C. to about 100° C., and more preferably about 50° C. to about 80° C., and most preferably about 55° C. to about 65° C. Preferable the drying is conducted for a period of about 8 to about 60 hours, more preferably about 20 to about 50 hours, and particularly about 30 to about 50 hours.

The present disclosure also relates to the use of the solid state forms of Omecamtiv mecarbil and Omecamtiv mecarbil diHCl of the present disclosure, for preparing other solid state forms of Omecamtiv mecarbil diHCl, Omecamtiv mecarbil and/or other Omecamtiv mecarbil salts and solid state forms thereof.

The present disclosure further provides solid state forms of Omecamtiv mecarbil and Omecamtiv mecarbil diHCl for use in the preparation of other solid state forms of Omecamtiv mecarbil diHCl, Omecamtiv mecarbil and/or other Omecamtiv mecarbil salts and solid state forms thereof.

The present disclosure also encompasses the use of the described solid state forms of Omecamtiv mecarbil and Omecamtiv mecarbil diHCl for the preparation of pharmaceutical compositions and/or formulations.

The present disclosure further encompasses processes for preparing salts of Omecamtiv mecarbil or solid state forms thereof. The process comprises preparing any crystalline form of the present disclosure (or a mixture thereof), and converting it to other solid state form of Omecamtiv mecarbil diHCl. Alternatively, the process comprises preparing any solid state form of the present disclosure (or a mixture thereof), and converting it to a salt of Omecamtiv mecarbil. The conversion can be done, for example, by a process comprising reacting the obtained Omecamtiv mecarbil with an appropriate acid to obtain the corresponding addition salt.

The present disclosure further encompasses the described solid state forms of Omecamtiv mecarbil and/or Omecamtiv mecarbil diHCl for use in the preparation of pharmaceutical compositions and/or formulations for use in medicine, preferably for the treatment of heart failure.

In another aspect, the present disclosure provides pharmaceutical compositions comprising the solid state forms according to the present disclosure.

In yet another embodiment, the present disclosure encompasses pharmaceutical formulations comprising the described solid state forms of Omecamtiv mecarbil and/or Omecamtiv mecarbil diHCl, or of pharmaceutical compositions comprising the solid state forms of Omecamtiv mecarbil and/or Omecamtiv mecarbil diHCl, and at least one pharmaceutically acceptable excipient.

The present disclosure further encompasses processes to prepare said pharmaceutical formulations of Omecamtiv mecarbil and Omecamtiv mecarbil diHCl comprising combining any of the above solid state forms of Omecamtiv mecarbil and/or Omecamtiv mecarbil diHCl or combination thereof) and at least one pharmaceutically acceptable excipient.

Pharmaceutical formulations of the present invention contain any one or a combination of the solid state forms of Omecamtiv mecarbil and Omecamtiv mecarbil diHCl of the present invention. In addition to the active ingredient, the pharmaceutical formulations of the present invention can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, the active ingredient and any other solid excipients are dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present invention, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present invention include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present invention is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present invention can be a capsule containing the composition, preferably a powdered or granulated solid composition of the invention, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, but they are not subjected to a final tableting step.

A pharmaceutical formulation of Omecamtiv mecarbil diHCl is preferably formulated for administration to a mammal, preferably a human. Omecamtiv mecarbil diHCl can be formulated, for example, as a viscous liquid solution or suspension, preferably a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The solid state forms as defined herein as well as the pharmaceutical compositions or formulations of the solid state forms of Omecamtiv mecarbil/Omecamtiv mecarbil diHCl may be used as medicaments, particularly for the treatment of heart failure.

The present disclosure also provides methods of treating heart failure comprising administering a therapeutically effective amount of any one or a combination of the above described solid state forms of Omecamtiv mecarbil/ Omecamtiv mecarbil diHCl, or at least one of the above pharmaceutical compositions or formulations, to a subject suffering from heart failure, or otherwise in need of the treatment.

The present disclosure also provides the use of any one (or a combination) of the solid state forms of the present disclosure, or at least one of the above pharmaceutical compositions or formulations, for the manufacture of medicaments for treating heart failure.

Having described the disclosure with reference to certain preferred embodiments, other embodiments will become apparent to one skilled in the art from consideration of the specification. The disclosure is further illustrated by reference to the following example describing in detail the preparation of the composition and methods of use of the disclosure. It will be apparent to those skilled in the art that many modifications, both to materials and methods, may be practiced without departing from the scope of the disclosure.

Analytical Methods

Powder X-Ray Diffraction Pattern ("PXRD") Method:

Sample after being powdered in a mortar and pestle is applied directly on a silicon plate holder. XRPD analysis was performed on ARL (SCINTAG) powder X-Ray diffractometer model X'TRA equipped with a solid state detector. Copper radiation of 1.5418 Å was used. Scanning parameters: range: 2-40 degrees two-theta; scan mode: continuous scan; step size: 0.05°, and a rate of 2 deg/min.

$^{13}$C Solid State NMR Method $^{13}$C CP/MAS NMR spectra were measured at 125 MHz using Bruker Avance III HD 500 US/WB NMR spectrometer (Karlsruhe, Germany, 2013). The $^{13}$C CP/MAS NMR spectra employing cross-polarization were acquired using the standard pulse scheme at spinning frequency of 11 kHz and controlled temperature at 293 K±3° C. A probe using 4 mm o.d. zirconia rotors was employed. The recycle delay was 6-60 s and the cross-polarization contact time was 1.75 ms. The strength of spin-locking fields $B_1(^{13}C)$ expressed in frequency units $w_1/2p=gB_1$ was 64 kHz. Chemical shifts were referenced via a replacement sample of glycine (carboxyl carbon chemical shift assigned as 176.03 ppm relative to the signal of tetramethyl silane).

EXAMPLES

The starting material Omecamtiv mecarbil, and Omecamtiv mecarbil diHCl can be prepared according to methods known from the literature (for example WO2006-009726, and WO2014-152270).

Example 1: Preparation of Form OCG-1 of Glycolic Omecamtiv Mecarbil diHCl

A solution of Omecamtiv mecarbil diHCl in double distilled water, 0.14 M, 620 µl (0.08 mmol, 40 mg) was placed in a 8 ml vial. To the above mixture, 746 µl (1.1 equiv., 0.09 mmol, 7 mg) of 0.125 M solution of glycolic acid in double distilled water was added and the reaction was stirred at room temperature overnight. Then, the above mixture was dried in a vacuum oven at 55° C. for additional 22 hours, during that time a pale yellow solid precipitated. Then, 10 V (400 µl) of tert-Butyl methyl ether (MTBE) were added and the mixture was stirred at room temperature for 18 hours. Finally, the reaction was filtered by centrifugation yielding a pale yellow solid which was characterized by X-ray powder diffraction to give the form OCG-1 of Glycolic Omecamtiv mecarbil diHCl (FIG. 1).

Example 2: Preparation of Form OCC-1 of Citric Omecamtiv Mecarbil diHCl

A solution of Omecamtiv mecarbil diHCl in double distilled water, 0.14 M, 620 µl (0.08 mmol, 40 mg) was placed in a 8 ml vial. To the above mixture, 746 µl (1.1 equiv., 0.09 mmol, 17.9 mg) of 0.125 M solution of citric acid in double distilled water was added and the reaction was stirred at room temperature overnight. Then, the above mixture was dried in a vacuum oven at 55° C. for additional 22 hours leading to yellowish oil. Then, 10 V (400 µl) of toluene were added and the mixture was stirred at room temperature for 18 hours, during that time a pale yellow solid precipitated. Finally, the reaction was filtered by centrifugation, yielding a pale yellow solid which was characterized by X-ray powder diffraction to give the form OCC-1 of Citric Omecamtiv mecarbil diHCl (FIG. 2).

Example 3: Preparation of Form OCM-1 of Malic Omecamtiv Mecarbil diHCl

A solution of Omecamtiv mecarbil diHCl in double distilled water, 0.14 M, 620 µl (0.08 mmol, 40 mg) was placed in a 8 ml vial. To the above mixture, 746 µl (1.1 equiv., 0.09 mmol, 12.5 mg) of 0.125 M solution of (L)-malic acid in double distilled water was added and the reaction was stirred at room temperature overnight. Then, the above mixture was dried in a vacuum oven at 55° C. for additional 48 hours, leading to a dry, pale yellow solid which was characterized by X-ray powder diffraction to give the form OCM-1 of Malic Omecamtiv mecarbil diHCl (FIG. 3).

Example 4: Preparation Form OCM-2 of Malic Omecamtiv Mecarbil diHCl

A solution of Omecamtiv mecarbil diHCl in double distilled water, 0.14 M, 620 µl (0.08 mmol, 40 mg) was placed in a 8 ml vial. To the above mixture, 746 µl (1.1 equiv., 0.09 mmol, 12.5 mg) of 0.125 M solution of (L)-malic acid in double distilled water was added and the reaction was stirred at room temperature overnight. Then, the above mixture was dried in a vacuum oven at 55° C. for additional 48 hours, during that time white solid precipitated. Then, 10 V (400 µl) of acetonitrile (ACN) were added and the mixture was stirred at room temperature for 18 hours. Finally, the reaction was filtered by centrifugation, yielding white solid which was characterized by X-ray powder diffraction to give the form OCM-2 of Malic Omecamtiv mecarbil diHCl (FIG. 4).

Example 5: Preparation of Form OCM-3 of Malonic Omecamtiv Mecarbil diHCl

A solution of Omecamtiv mecarbil diHCl in double distilled water, 0.14 M, 620 µl (0.08 mmol, 40 mg) was placed in a 8 ml vial. To the above mixture, 746 µl (1.1 equiv., 0.09 mmol, 9.7 mg) of 0.125 M solution of malonic acid in double distilled water was added. The above mixture was dried in a vacuum oven at room temperature for 12 hours and then at 55° C. for additional 16 hours, during that time pale yellow solid precipitated. Then, 10 V (400 µl) of ACN were added and the mixture was stirred at room temperature for 18 hours. Finally, the reaction was filtered by centrifugation, yielding pale yellow solid which was characterized by X-ray powder diffraction to give the form OCM-3 of Malonic Omecamtiv mecarbil diHCl malate (FIG. 5).

Example 6: Preparation of Form O-1 of Omecamtiv Mecarbil

Ethyl acetate (3 ml, 100V) was added to Omecamtiv mecarbil (30 mg, 0.075 mmol) to give slurry at room temperature. The obtained slurry was magnetically stirred and heated to 60° C. The hot slurry was stirred at 60° C. during 30 min to give clear solution. Then, the obtained clear solution was cooled to 3° C. and stirred at this temperature during about 30 minutes. Next, cold hexane (3 ml, 100V) was added to the obtained clear solution and magnetically stirred at 3° C. during about 1 hour to afford a solid precipitation. The obtained solid was filtered by centrifugation and dried in vacuum oven at 50° C. during about 18 hours. The dry solid was characterized by X-ray powder diffraction: Omecamtiv mecarbil form O-1.

Example 7: Preparation of Form O-1 of Omecamtiv Mecarbil

THF (2 ml, 66V) was added to Omecamtiv mecarbil (30 mg, 0.075 mmol) to give slurry at room temperature. The obtained slurry was magnetically stirred and heated to 60° C. to give clear solution. Then, the obtained hot clear solution was cooled to 3° C. and stirred at this temperature during about 30 minutes. Cold hexane (2 ml, 66V) was added to the stirred clear solution at 3° C. during about 1 hour to give a solid precipitation. The obtained solid was filtered by centrifugation and dried in vacuum oven at 50° C. during about 18 hours. The obtained dry solid was characterized by X-ray powder diffraction; form O-1 of Omecamtiv mecarbil; as shown in FIG. 6.

Example 8: Preparation of Form O-2 of Omecamtiv Mecarbil

MeOH (10 ml, 20V) was added to form O-1 of Omecamtiv mecarbil (0.5 g, 1.24 mmol) to give slurry at room temperature. The obtained slurry was magnetically stirred and heated to 60° C. during about 30 min to give clear solution. Then, the obtained clear solution was cooled to room temperature and stirred at this temperature during about 24 hours and precipitation occurred. The obtained precipitant was filtered by centrifugation. The obtained solid was characterized by X-ray powder diffraction –Omecamtiv mecarbil form O-2; as shown in FIG. 7.

Example 9: Preparation of Form O-2 of Omecamtiv Mecarbil

THF (600 µl, 20V) was added to form O-1 of Omecamtiv mecarbil (30 mg, 0.075 mmol) to give slurry at room temperature. The slurry was magnetically stirred and heated to 60° C. The slurry was stirred at this temperature over a period of 2 hours to give a clear solution. Next, the obtained clear solution was cooled to room temperature and precipitation occurred. The obtained precipitant was filtered by centrifugation and characterized by X-ray powder diffraction; form O-2 of Omecamtiv mecarbil.

Example 10: Preparation of Form O-3 of Omecamtiv Mecarbil

Dioxane (10 ml, 20V) was added to form O-1 of Omecamtiv mecarbil (0.5 g, 1.24 mmol) to give slurry at room temperature. The obtained slurry was stirred and heated to 95° C. over a period of about 30 minutes to give a clear solution. The obtained clear solution was cooled to room temperature and stirred at this temperature during about 24 hours. The obtained precipitant was isolated by separation in centrifuge. The obtained solid was characterized by X-ray powder diffraction as Omecamtiv mecarbil form O-3 (FIG. 8).

Example 11: Preparation of Form O-4 of Omecamtiv Mecarbil

Form O-3 of Omecamtiv mecarbil (100 mg, 0.25 mmol) was placed in vacuum oven at 60° C. over a period of 48 hours. The obtained solid was characterized by X-ray powder diffraction as Omecamtiv mecarbil free base form O-4 (FIG. 9).

Example 12: Preparation of Form O-S1 Omecamtiv Mecarbil diHCl

Propionic acid (600 µL) was added to Omecamtiv mecarbil diHCl (30 mg, 0.63 mmol) to give slurry at room temperature. The slurry was heated and magnetically stirred at 90° C. over a period of about 12 hours followed by heating to 120° C. and stirring at this temperature during about 2 hours. Then, the slurry was cooled to room temperature and isolated by using centrifuge. The isolated solid was characterized by X-ray powder diffractogram as Omecamtiv mecarbil diHCl form O-S1 (FIG. 10).

Example 13: Preparation of Form O-S2 of Omecamtiv Mecarbil diHCl

Acetic acid (600 µL, 20V) was added to Omecamtiv mecarbil diHCl (30 mg, 0.63 mmol) to give slurry at room temperature. The slurry was heated and magnetically stirred at 90° C. over a period of about 12 hours followed by heating to 120° C. and stirring at this temperature during about 2 hours to give clear solution. The obtained clear solution was cooled to room temperature and precipitation occurred. The obtained precipitant was filtered using centrifuge. The obtained solid was characterized by X-ray powder diffractogram as Omecamtiv mecarbil diHCl form O-S2 (FIG. 11).

Example 14: Preparation of Form O-S3 of Omecamtiv Mecarbil diHCl

Omecamtiv mecarbil diHCl (30 mg, 0.63 mmol) was placed in a glass tube. The tube was inserted to 20 ml vial filled with 2 ml of butyric acid. The 20 ml vial was tightly closed for 1 week at room temperature. Next, the sample was characterized by X-ray powder diffractogram as Omecamtiv mecarbil diHCl form OS-3 as depicted in FIG. 12.

Example 15: Preparation of Form O-S4 of Omecamtiv Mecarbil diHCl

Propionic acid (600 µL, 20V) was added to Omecamtiv mecarbil diHCl (30 mg, 0.63 mmol) to give slurry at room temperature. The obtained slurry was magnetically stirred at room temperature during about 18 hours. Then, the slurry was filtered by centrifuge. The obtained solid was characterized by X-ray powder diffractogram as Omecamtiv mecarbil diHCl form O-S4 (FIG. 13).

Example 16: Preparation of Form O-S5 of Omecamtiv Mecarbil diHCl

Acetic acid (600 µL, 20V) was added to Omecamtiv mecarbil diHCl form A (30 mg, 0.63 mmol) to give slurry at room temperature. The slurry was magnetically stirred at room temperature for about 12 hours. Next, the slurry was separated by centrifuge. The isolated solid was characterized by X-ray powder diffractogram as Omecamtiv mecarbil diHCl form O-S5 (FIG. 14).

Example 17: Preparation of Omecamtiv Mecarbil diHCl Amorphous Form

Water (20 g, 13.33V) was added to Omecamtiv mecarbil diHCl form A (1.5 g, 42.15 mmol) to give diluted slurry at room temperature. The obtained diluted slurry was stirred at room temperature to give clear solution. The obtained clear solution was dried by spray dryer. The obtained solid was characterized by X-ray powder diffraction as amorphous Omecamtiv mecarbil diHCl (FIG. 15).

Example 18: Preparation of Omecamtiv Mecarbil diHCl Amorphous Form

Omecamtiv mecarbil diHCl (5 g, 10.54 mmol) was dissolved in water (100 g, 20V) at room temperature. The obtained solution was mechanically filtrated (micro disk filter with pores of 0.2 micron). The obtained clear solution was lyophilized upon −40° C. to 25° C. to give solid, which was characterized by X-ray powder diffraction as amorphous Omecamtiv mecarbil diHCl (FIG. 16).

Example 19: Preparation of Form OCM-3 of Malonic Omecamtiv Mecarbil diHCl

Omecamtiv mecarbil diHCl (50 mg, 0.105 mmol) was grinded by mortar and pestle with malonic acid (13 mg, 0.125 mg) in a presence of 1 drop water at room temperature, during 3 minutes. The obtained solid was characterized by X-ray powder diffraction as form OCM-3 of Malonic Omecamtiv mecarbil diHCl.

Example 20: Preparation of Form OCM-3 of Malonic Omecamtiv Mecarbil diHCl

Chloroform (0.64 ml, 10V) was added to Omecamtiv mecarbil diHCl (50 mg, 0.105 mmol) and malonic acid (13 mg, 0.125 mg, 1.19 eqv.) to give slurry at room temperature. The obtained slurry was magnetically stirred at room temperature during 48 hours. Next, the solid was separated using centrifuge and dried in vacuum oven at 45° C. during 4 hours. The obtained dry solid was characterized by X-ray powder diffraction as form OCM-3 of Malonic Omecamtiv mecarbil diHCl.

Example 21: Preparation of OCM-3 of Malonic Omecamtiv Mecarbil diHCl

A solution of Omecamtiv mecarbil diHCl (2 g) in double distilled water (31.2 ml) was placed in a flask. To the this mixture, a solution of malonic acid in double distilled water was added (0.5 g in 38.6 ml) and the reaction mixture (clear solution) was stirred at room temperature for 15 minutes. The obtained mixture was dried in a vacuum oven at 55° C. during 48 hours to give a yellowish solid, which was characterized by X-ray powder diffraction as form OCM-3 of Malonic Omecamtiv mecarbil diHCl.

Example 22: Preparation of Form OCC-1 of Citric Omecamtiv Mecarbil diHCl

A solution of Omecamtiv mecarbil diHCl (2 g) in double distilled water (31.2 ml) was placed in a flask. A solution of citric acid in double distilled water was added (0.929 g in 38.6 ml) was added and the reaction mixture (clear solution) was stirred at room temperature for 15 minutes. The mixture was then dried in a vacuum oven at 55° C. for 48 hours to give yellowish solid, which was characterized by X-ray powder diffraction as form OCC-1 of Citric Omecamtiv mecarbil diHCl.

The invention claimed is:

1. A crystalline form of Citric Omecamtiv mecarbil diHCl designated as form OCC-1, characterized by data selected from one or more of the following:
   a. an XRPD pattern having peaks at 14.6, 15.6, 16.7, 24.5 and 25.1 degrees two theta±0.2 degrees two theta;
   b. an XRPD pattern as depicted in FIG. 2; or
   c. an XRPD pattern having peaks at 14.6, 15.6, 16.7, 24.5 and 25.1 degrees two theta±0.2 degrees two theta, and also having one, two, three, four or five additional peaks selected from 15.4, 19.2, 20.9, 23.5 and 29.6 degrees two theta±0.2 degrees two theta.

2. A crystalline form of Crystalline Malonic Omecamtiv mecarbil diHCl designated as form OCM-3, characterized by data selected from one or more of the following:
   a. an XRPD pattern having peaks at 6.0, 16.2, 17.2, 24.3 and 25.7 degrees two theta±0.2 degrees two theta;
   b. an XRPD pattern as depicted in FIG. 5; or
   c. an XRPD pattern having peaks at 6.0, 16.2, 17.2, 24.3 and 25.7 degrees two theta±0.2 degrees two theta, and also having one, two, three, four or five additional peaks selected from 12.1, 18.2, 19.0, 21.4 and 28.3 degrees two theta±0.2 degrees two theta.

3. A process for preparing a crystalline form of Citric Omecamtiv mecarbil diHCl according to claim 1, wherein the process comprises the following steps:
   (i) providing a mixture comprising Omecamtiv mecarbil diHCl and citric acid in water;
   (ii) optionally stirring the mixture;
   (iii) at least partially removing the water; and optionally adding a non-protic solvent; and
   (vi) isolating the crystalline form.

4. A process according to claim 3 further comprising combining the crystalline form of Citric Omecamtiv mecarbil diHCl with at least one pharmaceutically acceptable excipient to provide a pharmaceutical composition or formulation.

5. A crystalline Citric Omecamtiv mecarbil diHCl obtainable by the process of claim 3.

6. A pharmaceutical composition or formulation comprising crystalline Citric Omecamtiv mecarbil diHCl according to claim 1.

7. A pharmaceutical composition or formulation according to claim 6 comprising at least one pharmaceutically acceptable excipient.

8. A process for preparing a pharmaceutical composition or formulation according to claim 6 comprising combining crystalline Citric Omecamtiv mecarbil diHCl and at least one pharmaceutically acceptable excipient.

9. A method of treating heart failure, comprising administering an effective amount of crystalline Citric Omecamtiv mecarbil diHCl according to claim 1 to a subject suffering from heart failure, or otherwise in need of the treatment.

10. A process for preparing a crystalline form of Malonic Omecamtiv mecarbil diHCl according to claim 2, wherein the process comprises the following steps:
  (i) providing a mixture comprising Omecamtiv mecarbil diHCl and malonic acid in water;
  (ii) optionally stirring the mixture;
  (iii) at least partially removing the water; and optionally adding a non-protic solvent; and
  (vi) isolating the crystalline form.

11. A process according to claim 10 further comprising combining the crystalline form of Malonic Omecamtiv mecarbil diHCl with at least one pharmaceutically acceptable excipient to provide a pharmaceutical composition or formulation.

12. A crystalline Malonic Omecamtiv mecarbil diHCl obtainable by the process of claim 10.

13. A pharmaceutical composition or formulation comprising crystalline Malonic Omecamtiv mecarbil diHCl according to claim 2.

14. A pharmaceutical composition or formulation according to claim 13 comprising at least one pharmaceutically acceptable excipient.

15. A process for preparing a pharmaceutical composition or formulation according to claim 13 comprising combining crystalline Malonic Omecamtiv mecarbil diHCl and at least one pharmaceutically acceptable excipient.

16. A method of treating heart failure, comprising administering an effective amount of crystalline Malonic Omecamtiv mecarbil diHCl according to claim 2 to a subject suffering from heart failure, or otherwise in need of the treatment.

* * * * *